(12) United States Patent
Nguyen et al.

(10) Patent No.: US 7,856,741 B2
(45) Date of Patent: *Dec. 28, 2010

(54) ADJUSTABLE ORTHOPEDIC DEVICE

(76) Inventors: Phu Nguyen, 7655 71st Ave., Pinellas Park, FL (US) 33781; Timothy A. Freriks, 10504 Carrollview Dr., Tampa, FL (US) 33618

( * ) Notice: Subject to any disclaimer, the term of this patent is extended or adjusted under 35 U.S.C. 154(b) by 868 days.

This patent is subject to a terminal disclaimer.

(21) Appl. No.: 11/761,587

(22) Filed: Jun. 12, 2007

(65) Prior Publication Data
US 2008/0307677 A1 Dec. 18, 2008

(51) Int. Cl.
*A61F 5/14* (2006.01)
(52) U.S. Cl. .............................. 36/155; 36/160; 36/161
(58) Field of Classification Search .................. 36/155, 36/159, 160, 161, 163, 164, 174, 180, 181, 36/152, 71; 602/29, 66, 30
See application file for complete search history.

(56) References Cited

U.S. PATENT DOCUMENTS

| | | | | | |
|---|---|---|---|---|---|
| 1,061,353 | A | * | 5/1913 | Block | 36/163 |
| 1,098,397 | A | * | 6/1914 | Pecorella | 602/30 |
| 1,538,026 | A | | 5/1925 | Cramer | |
| 1,741,340 | A | | 12/1929 | Scholl | |
| 1,746,865 | A | * | 2/1930 | Page | 602/30 |
| 1,767,263 | A | | 6/1930 | Scholl | |
| 1,952,538 | A | * | 3/1934 | Devine | 36/164 |
| 2,573,363 | A | | 10/1951 | Ruddick | |
| 2,633,129 | A | * | 3/1953 | Crawford | 602/66 |
| 2,835,248 | A | * | 5/1958 | Scholl | 602/30 |
| 3,086,520 | A | | 4/1963 | Scholl | |
| 4,227,320 | A | * | 10/1980 | Borgeas | 36/88 |
| 4,316,333 | A | | 2/1982 | Rothschild | |
| 4,510,699 | A | * | 4/1985 | Nakamura et al. | 36/43 |
| 4,745,927 | A | * | 5/1988 | Brock | 36/140 |
| 4,841,648 | A | * | 6/1989 | Shaffer et al. | 36/43 |
| 5,477,625 | A | * | 12/1995 | Goldsmith et al. | 36/36 R |
| 5,755,679 | A | * | 5/1998 | Selner et al. | 602/27 |
| 6,000,147 | A | * | 12/1999 | Kellerman | 36/44 |
| 6,205,685 | B1 | | 3/2001 | Kellerman | |
| 6,228,045 | B1 | * | 5/2001 | Gaylord et al. | 602/27 |
| 7,210,250 | B2 | * | 5/2007 | Gallegos | 36/44 |
| 7,644,522 | B2 | * | 1/2010 | Ramirez | 36/160 |
| 2005/0287500 | A1 | * | 12/2005 | Hubbard | 434/150 |
| 2006/0156603 | A1 | * | 7/2006 | Richards | 40/665 |
| 2008/0307678 | A1 | * | 12/2008 | Nguyen et al. | 36/155 |

* cited by examiner

*Primary Examiner*—Marie Patterson
(74) *Attorney, Agent, or Firm*—Larson & Larson, P.A.; Frank Liebenow

(57) ABSTRACT

An application for an adjustable orthopedic device includes a holder configured to be worn on a wearer's foot. The holder has an elastic cloth band sized to encircle the wearer's foot at a location between the wearer's toes and the wearer's ankle. The holder also has a holding strap affixed to the elastic cloth band, the holding strap securely holds a platform beneath the wearer's foot. The platform is positioned beneath the wearer's foot and includes a magnetic material. Raised pads are provided for applying pressure to one or more bones of the wearer's foot, the raised pads include a ferromagnetic material providing a removable adherence to the platform through magnetic force and allowing the raised pads to be manually repositionable to any X and Y coordinate on the platform.

18 Claims, 14 Drawing Sheets

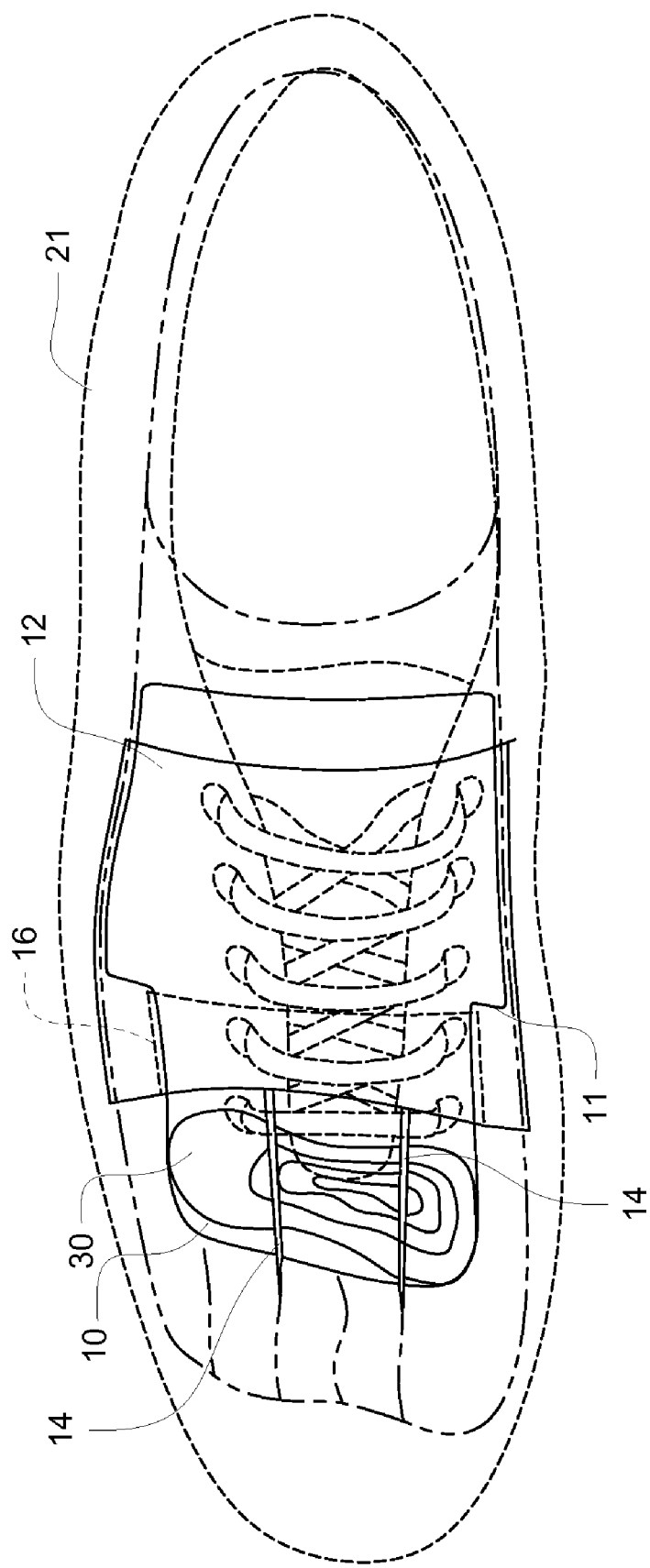

ADJUSTABLE ORTHOPEDIC DEVICE

FIELD OF THE INVENTION

This invention relates to the field of orthopedic devices for insertion into one's shoes and more particularly to a platform for accurately placing and holding orthopedic aids.

BACKGROUND OF THE INVENTION

Many traumatic conditions of the foot are caused by the misalignment of the joints in the foot. Such conditions can be hereditary or can be caused by an accident or repetitive stress. No matter the cause, people who suffer from such ailments are often in pain during normal activities such as walking and exercising. In some cases, the condition is so bad; it causes excruciating pain to the extent a person cannot walk without an orthopedic aid.

Often, the solution to the problem is to provide a contoured surface under the patient's foot, thereby redistributing the force of the wearer's weight over different areas of the foot or raising a toe to its normal posture, etc. Prior solutions to this problem included providing a shoe with an integrated, prescription form, compensation for the malformed foot. Unfortunately, such a solution is not cost-effective because the prescribed form must be present in all shoes used by the patient. Furthermore, it is often difficult to form the precise lifts in the precise location as needed. Once the shoe is made, if it doesn't fix the problem, there is no way to adjust lifts within the shoe.

A solution to this problem is proposed in U.S. Pat. No. 6,205,685 to Kellerman and is hereby incorporated by reference. This patent has a shoe insert that has an adhesive on its surface where it contacts the shoe's inner sole. The opposite side is covered with loop material (e.g., Velcro®). Once installed on the inner sole, one or more pads having hook material on their bottom surface are positioned on the loop material. The solution presented in this patent has several problems. First, it is extremely difficult to accurately position the pads using the hook and loop material. Second, the described device is permanently installed into the user's shoe, requiring a device for each shoe the user owns. Third, hook and loop material and the adhesive bottom surface are generally thick, causing crowding of the foot in many shoes. Finally, for those with severe problems where they cannot walk without the prescribed device, it is extremely difficult to try on new shoes that are absent the prescribed platform.

Another solution to this problem is proposed in U.S. Pat. No. 4,316,333 to Rothschild. This too has a pressure-sensitive element with hook or loop material and engaging elements with hook or loop materials that are positioned on the pressure-sensitive element within the shoe. This solution has several problems similar to the prior patent. First, it is extremely difficult to accurately position the pads using the hook and loop material. Second, the described device is permanently installed into the user's shoe, requiring a device for each shoe the user owns. Third, hook and loop material and the adhesive bottom surface are generally thick, causing crowding of the foot in many shoes. Finally, for those with severe problems where they cannot walk without the prescribed device, it is extremely difficult to try on new shoes that are absent the prescribed platform.

Another solution is proposed in U.S. Pat. No. 2,573,363 to Ruddick. This patent proposes a band that wraps around the user's foot and has toe straps that go between the user's toes, thereby holding the band in place within the user's shoe. The engaging elements are directly attached to the band. This solution addresses several of the problems such as being worn on the foot instead of installed in the shoe, therefore, one device can be used with multiple shoes. Still, this patent is not a complete solution. Unfortunately, this device is made with pads in specific locations, making adjustment impossible.

What is needed is an adjustable orthopedic solution that provides a platform for securely and accurately affixing one or more orthopedic elements in position beneath the effected bone.

SUMMARY OF THE INVENTION

In one embodiment, an adjustable orthopedic device is disclosed a holder configured to be worn on a wearer's foot and a platform adapted to the holder and positioned beneath the wearer's foot. One or more raised pads are provided for applying pressure to one or more bones of the wearer's foot. The raised pads are removably affixed to the platform through magnetic force making them manually repositionable to any X and Y coordinate on the platform by the wearer.

In another embodiment, an adjustable orthopedic device is disclosed including a holder configured to be worn on a wearer's foot. The holder has an elastic cloth band sized to encircle the wearer's foot at a location between the wearer's toes and the wearer's ankle. The holder also has a holding strap affixed to the elastic cloth band, the holding strap securely holds a platform beneath the wearer's foot. The platform is positioned beneath the wearer's foot and includes a magnetic material. Raised pads are provided for applying pressure to one or more bones of the wearer's foot, the raised pads include a ferromagnetic material providing a removable adherence to the platform through magnetic force and allowing the raised pads to be manually repositionable to any X and Y coordinate on the platform.

In another embodiment, an adjustable orthopedic device is disclosed including a platform positioned beneath a wearer's foot and one or more raised pads removably affixed to the platform, whereas the one or more raised pads are manually repositionable to any X and Y coordinate on the platform.

BRIEF DESCRIPTION OF THE DRAWINGS

The invention can be best understood by those having ordinary skill in the art by reference to the following detailed description when considered in conjunction with the accompanying drawings in which:

FIG. 1B illustrates a top schematic view of a system of the first embodiment of the present invention.

DETAILED DESCRIPTION OF THE INVENTION

Figure 1A:
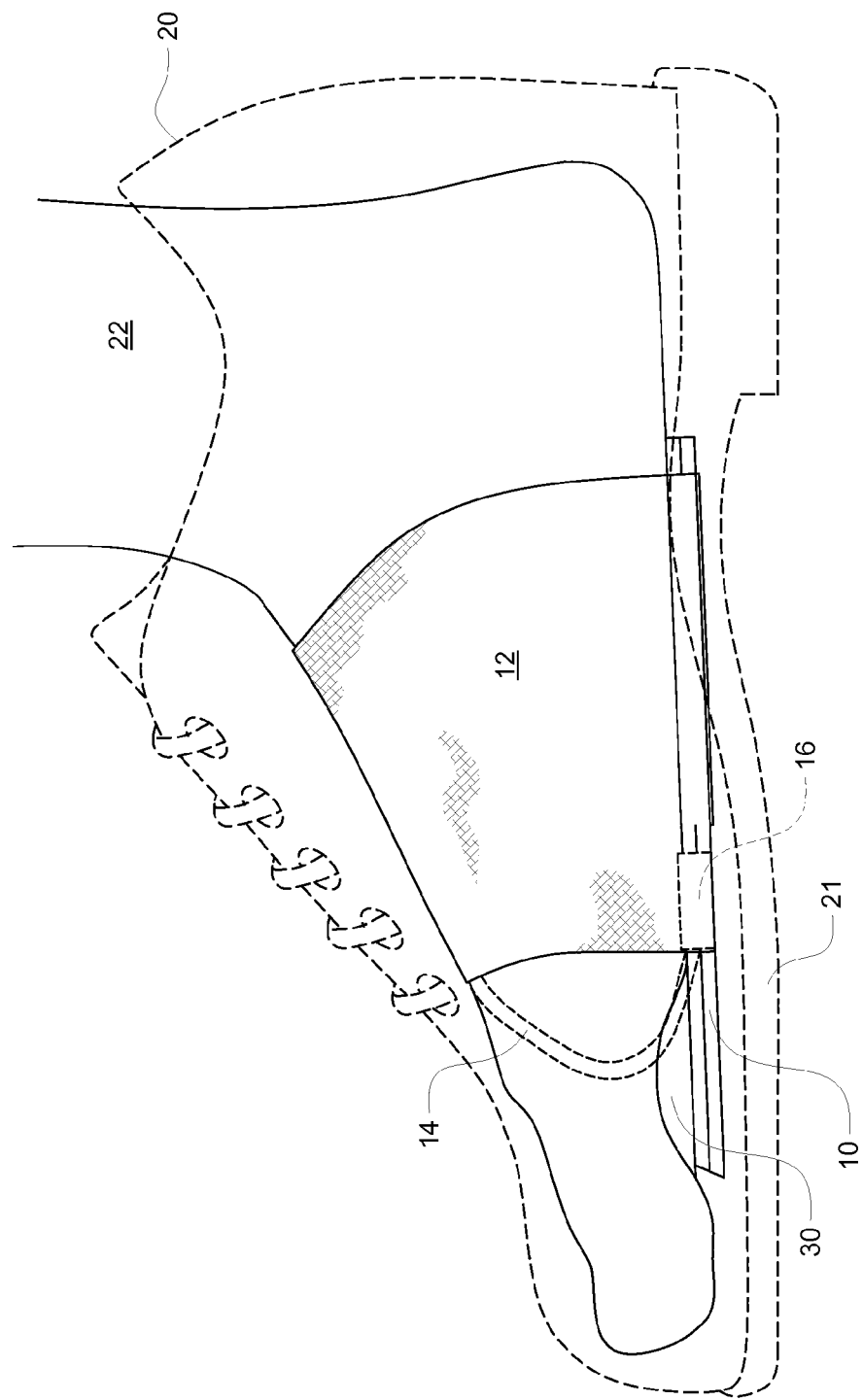
FIG. 1A illustrates a side schematic view of a system of a first embodiment of the present invention.

Reference will now be made in detail to the presently preferred embodiments of the invention, examples of which are illustrated in the accompanying drawings. Throughout the following detailed description, the same reference numerals refer to the same elements in all figures.

Referring to FIG. 1A, a side schematic view of a system of a first embodiment of the present invention will be described. Often, to combat orthopedic problems, a doctor recommends or prescribes a remedy that includes placing pads or raised areas beneath affected areas of the foot. Past solutions included prescription shoes with such raised areas integrated into the curvature of the inner sole of the shoe. Unfortunately, such a solution requires the prescription to be replicated across all shoes the wearer owns. Furthermore, once manufactured, it is difficult to make any fine adjustments.

The solution of the present invention includes a platform 10 and one or more raised pads 30 that stick to the platform 10 and are easily adjusted by swapping with other raised pads 30 or by manually repositioning the raised pads along the X and Y axis upon the platform 10. In the preferred embodiment, the raised pads 30 are held to the platform 10 by magnetic force, either having a magnet integrated into the bottom of the raised pads 30 and using a ferromagnetic material such as iron or steel for the platform 10; having a magnetic material integrated into the bottom of the raised pads 30 and using a ferromagnetic material for the platform 10; or using a magnetic material for both the bottom of the raised pads 30 and the platform 10. In some embodiments, the magnet is a solid magnet. In other embodiments, the magnet is flexible, made from powdered iron as known in the industry. In some embodiments, the platform 10 is covered on the bottom by a plastic coating or plastic sheet to prevent tearing and wear on the shoe. In some embodiments, the platform 10 is coated with a sticky or tacky surface to reduce movement within the wearer's shoe.

Figure 2:
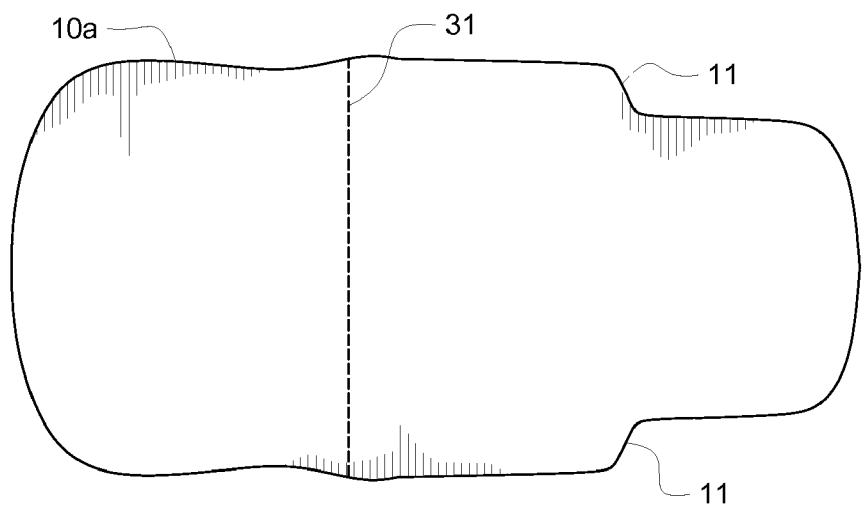
FIG. 2 illustrates a plan view of the first embodiment of the present invention.

In the preferred embodiment, the platform 10 is held within an anchor strap 16 of a holder that is worn like a sock around the wearer's foot 22. The holder includes a stretch strap or cloth elastic band 12 that is worn around the wearer's foot between the toes and the ankle. In the preferred embodiment, one or more toe straps 14 connect between top forward edges of the strap 12, pass between the wearer's toes and connect to the bottom forward edges of the strap 12. The toe straps 14 keep the holder from rotating around the wearer's foot 22 and keep it from sliding back within the wearer's shoe 20 while walking. The platform 10 slides into the holding strap 16 and is kept from moving forward by making notches 11 as shown in FIGS. 1B and 2. The platform 10 is sandwiched between the bottom of the wearer's foot 22 and the sole 21 of the shoe 20. Being that the holding strap 12 secures the holder to the wearer's foot 22, the wearer can change between shoes, try on new shoes, etc. without needing additional devices.

Referring to FIG. 1B, a top schematic view of a system of the first embodiment of the present invention will be described. The platform 10 is held within an anchor strap 16 of a holder that is worn like a sock around the wearer's foot. The holder includes a stretch strap 12 that is worn around the wearer's foot at a location between the toes and the ankle. In the preferred embodiment, one or more toe straps 14 connect between top forward edges of the strap 12, pass between the wearer's toes and connect to the bottom forward edges of the strap 12. The toe straps 14 keep the holder from rotating around the wearer's foot 22 and keep it from sliding back within the wearer's shoe 20 while walking. The platform 10 slides into the holding strap 16 and is kept from moving forward by making the holding strap 16 smaller than the larger width of the platform 10 at a notch or inflection point 11. Being that the holding strap 12 secures the holder to the wearer's foot 22, the wearer can change between shoes, try on new shoes, etc. without needing additional devices. One or more raised pads 30 are held to the platform 10 and are easily adjusted by swapping with other raised pads 30 or by manually repositioning the raised pads along the X and Y axis upon the platform 10. In the preferred embodiment, the raised pads 30 are held to the platform 10 by magnetic force, either having a magnet integrated into the bottom of the raised pads 30 and using a ferromagnetic material for the platform 10; having a magnetic material integrated into the bottom of the raised pads 30 and using a ferromagnetic material for the platform 10; or using a magnetic material for both the bottom of the raised pads 30 and the platform 10.

Referring to FIG. 2, a plan view of the magnetic platform 10a of the first embodiment of the present invention will be described. In this embodiment, the magnetic platform 10a is sized to accommodate both metatarsal pads and toe crest (or buttress) pads. The magnetic platform 10a has a narrow area (the area forward of the notch 11) that fits within the holding strap 16 (see FIG. 1) while the wider area (the area rear of the notch 11) keeps the magnetic platform 10a from pushing forward as the wearer walks. In some embodiments, a cut line 31 is provided to guide the user in cutting unneeded sections of the magnetic platform 10a. If the user needs only a toe crest pad, the back area of the magnetic platform 10a is cut along the cut line 31 and removed.

Figure 2A:
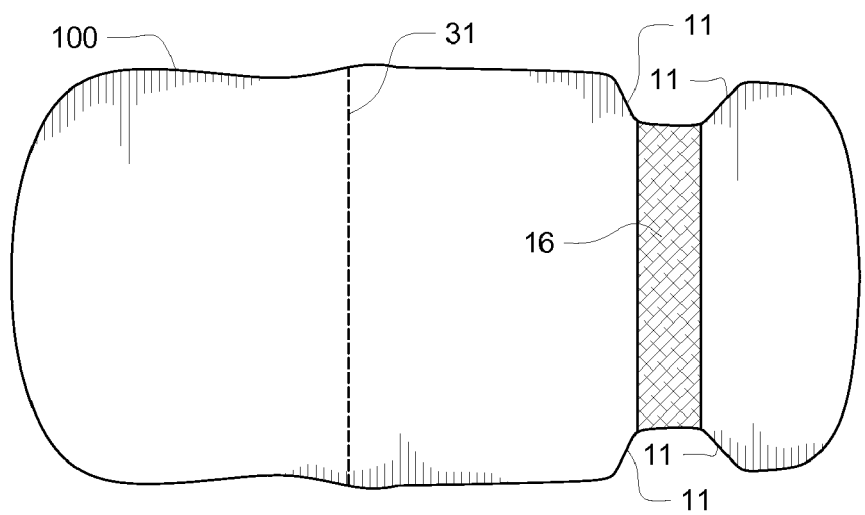
FIG. 2A illustrates a plan view of an alternate design of the first embodiment of the present invention.

Referring to FIG. 2A, a plan view of the magnetic platform 100 of an alternate design of the first embodiment of the present invention will be described. In this embodiment, the magnetic platform 100 is sized to accommodate both metatarsal pads and toe crest (or buttress) pads. The magnetic platform 100 has a narrow area (the area between the notches 11) that fits within the holding strap 16 which keeps the magnetic platform 100 from pushing forward, pushing rearward or twisting as the wearer walks. In some embodiments, a cut line 31 is provided to guide the user in cutting unneeded sections of the magnetic platform 100. If the user needs only a toe crest pad, the back area of the magnetic platform 100 is cut along the cut line 31 and removed.

Figure 3:
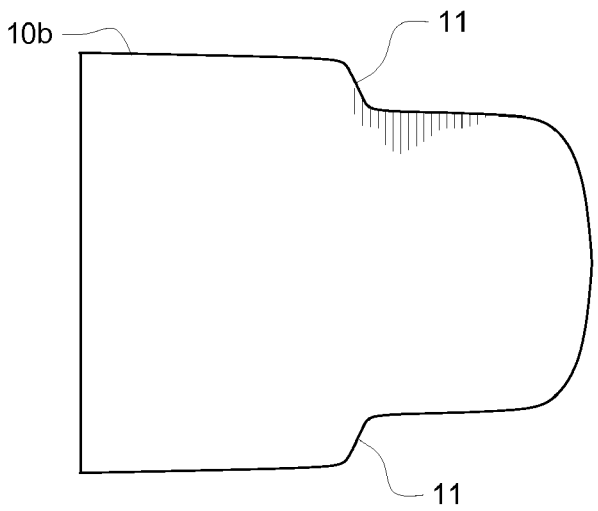
FIG. 3 illustrates a plan view of a second embodiment of the present invention.

Referring to FIG. 3, a plan view of a magnetic platform 10b of the second embodiment of the present invention will be described. In this embodiment, the magnetic platform 10b is sized to accommodate only toe crest (or buttress) pads. The magnetic platform 10b has a narrow area (the area forward of the notch 11) that fits within the holding strap 16 (see FIG. 1) while the wider area (the area rear of the notch 11) keeps the magnetic platform 10b from pushing forward as the wearer walks.

Figure 4:
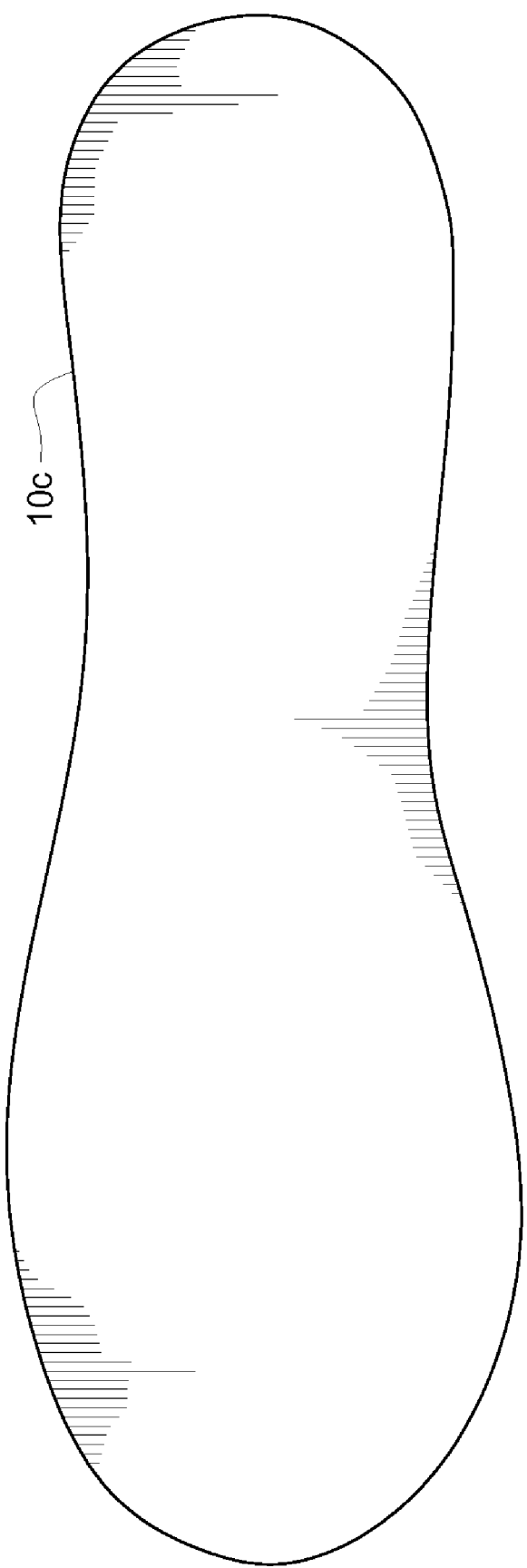
FIG. 4 illustrates a plan view of a third embodiment of the present invention.

Referring to FIG. 4, a plan view of the magnetic platform 10c of the third embodiment of the present invention will be described. In this embodiment, the magnetic platform 10c is sized to fit snuggly within a predetermined shoe such as a insole would fit. It is anticipated that several different sizes of the magnetic platform 10c will be provided for different shoe sizes or a larger magnetic platform 10c will be provided with cut lines provided to guide the user or doctor in trimming the magnetic platform 10c to the desired shoe size. The magnetic platform 10c is designed to accommodate any combination of metatarsal pads, toe crest (or buttress) pads and/or arch support pads.

FIGS. 5-10 show different combinations of metatarsal pads 30/32/34 and toe crest (or buttress) pads 40/42/44, each pad sized and shaped to remedy a particular bone problem of the user's foot. It is anticipated that many different metatarsal pads and toe crest (or buttress) pads will be provided with varying degrees of height and contour and the orthopedic doctor will determine the right pad for the particular ailment. The magnetic platform 10 provides for the ability to uniquely and adjustably position the selected pad(s) at any location to remedy the unique ailment of the individual patients. For reference, the metatarsal bones and phalanges are numbered, the bones of the big toe 80 being numbered 1 and the bones of the little toe 82 being numbered 5.

Figure 5:
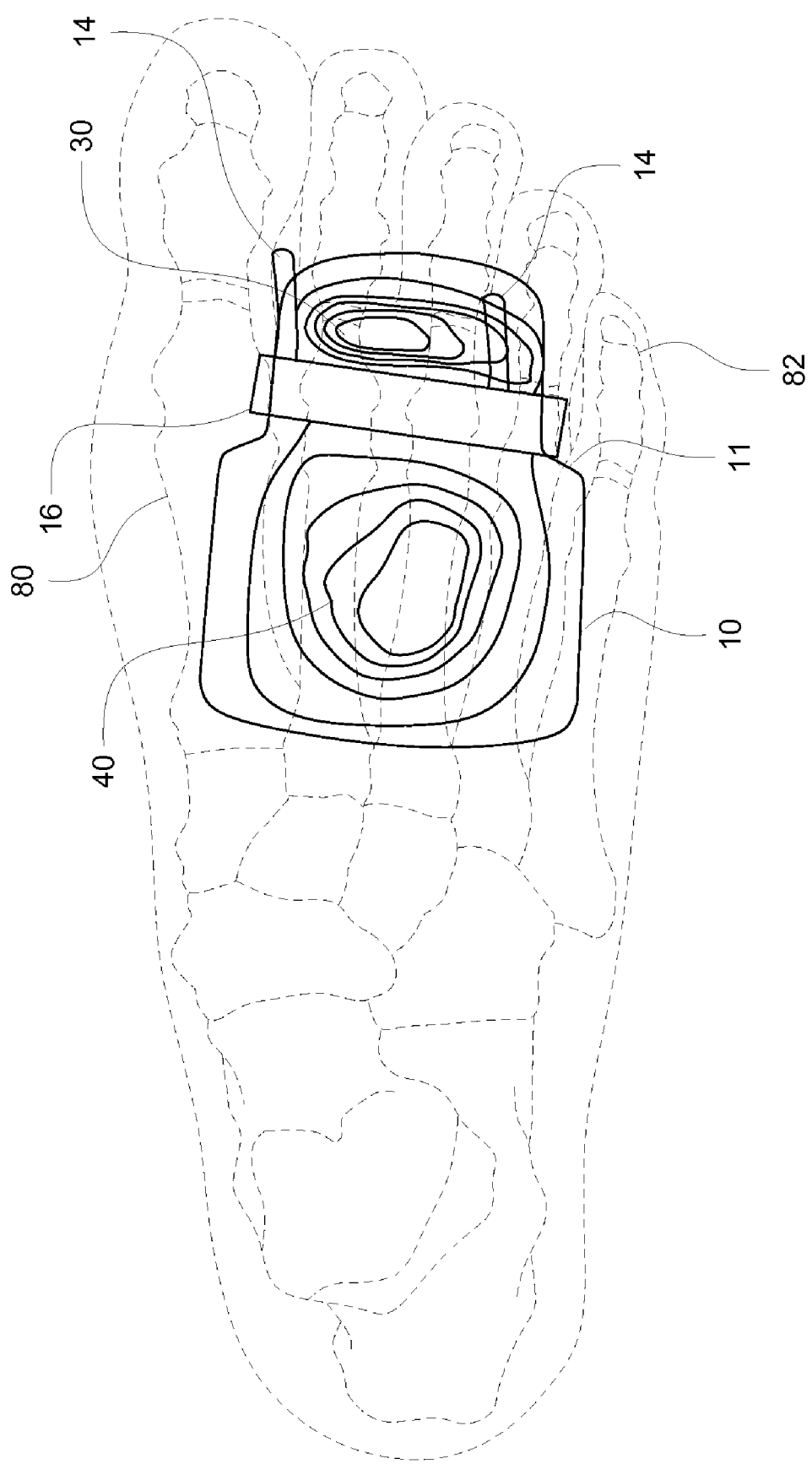
FIG. 5 illustrates a top plan view of the first and second embodiments of the present invention.
Figure 6:
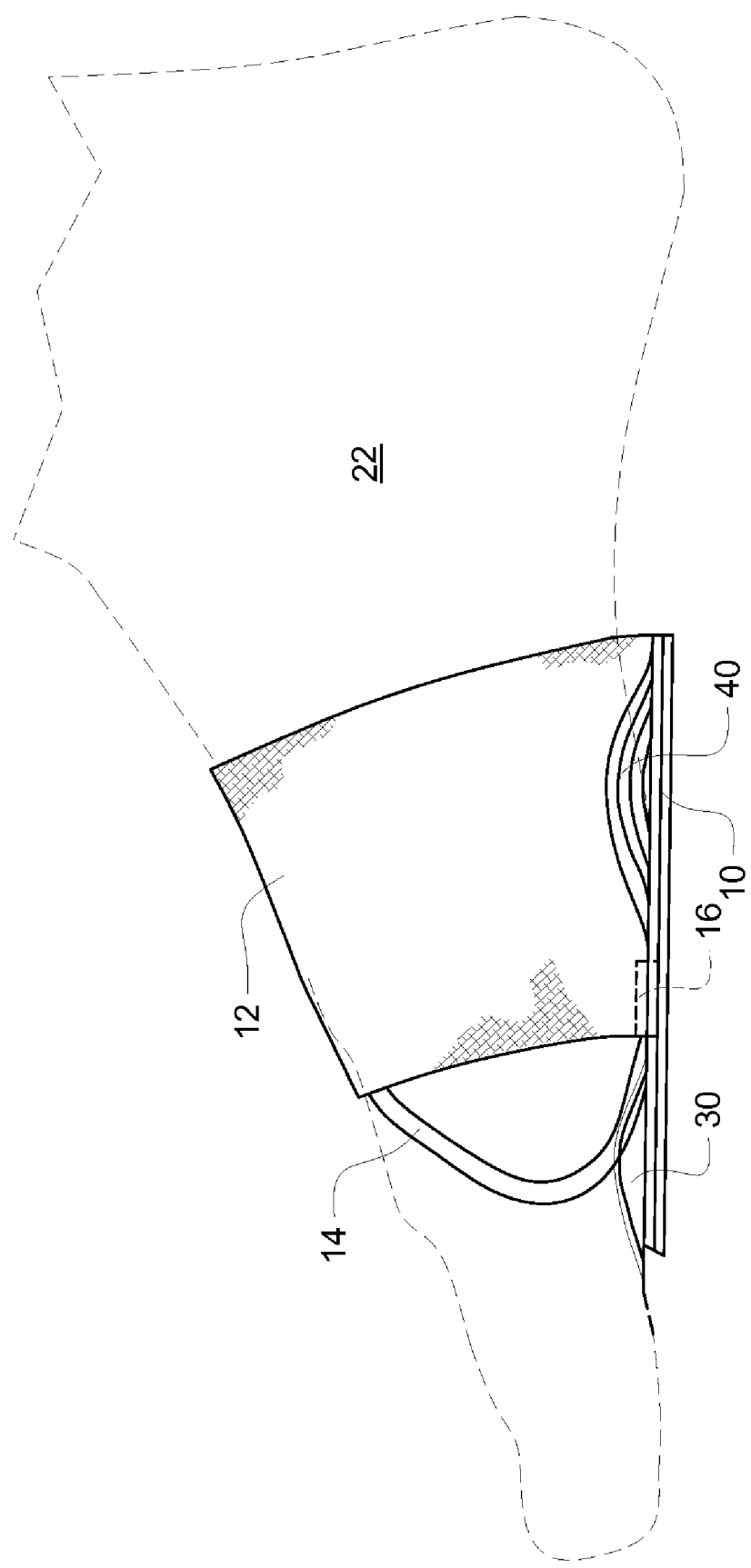
FIG. 6 illustrates a side plan view of the first and second embodiments of the present invention.

Referring to FIGS. 5 and 6, a top and side plan view of the first and second embodiments of the present invention will be described. The magnetic platform 10 is installed in the holding strap 16 and held to the wearer's foot 22 by the elastic cloth band 12 (shown in FIG. 6). The toe straps 14 limit the amount of rotation and front/back movement of the elastic cloth band, thereby holding the magnetic platform 10 in a relatively stable position with respect to the wearer's foot 22. In the example shown in FIG. 5, a metatarsal pad 40 is in place on the magnetic platform 10 to compensate for a problem with the fourth metatarsal bone and a toe crest pad 30 is in place on the magnetic platform 10 to compensate for a problem with the second phalange bone.

Figure 7:
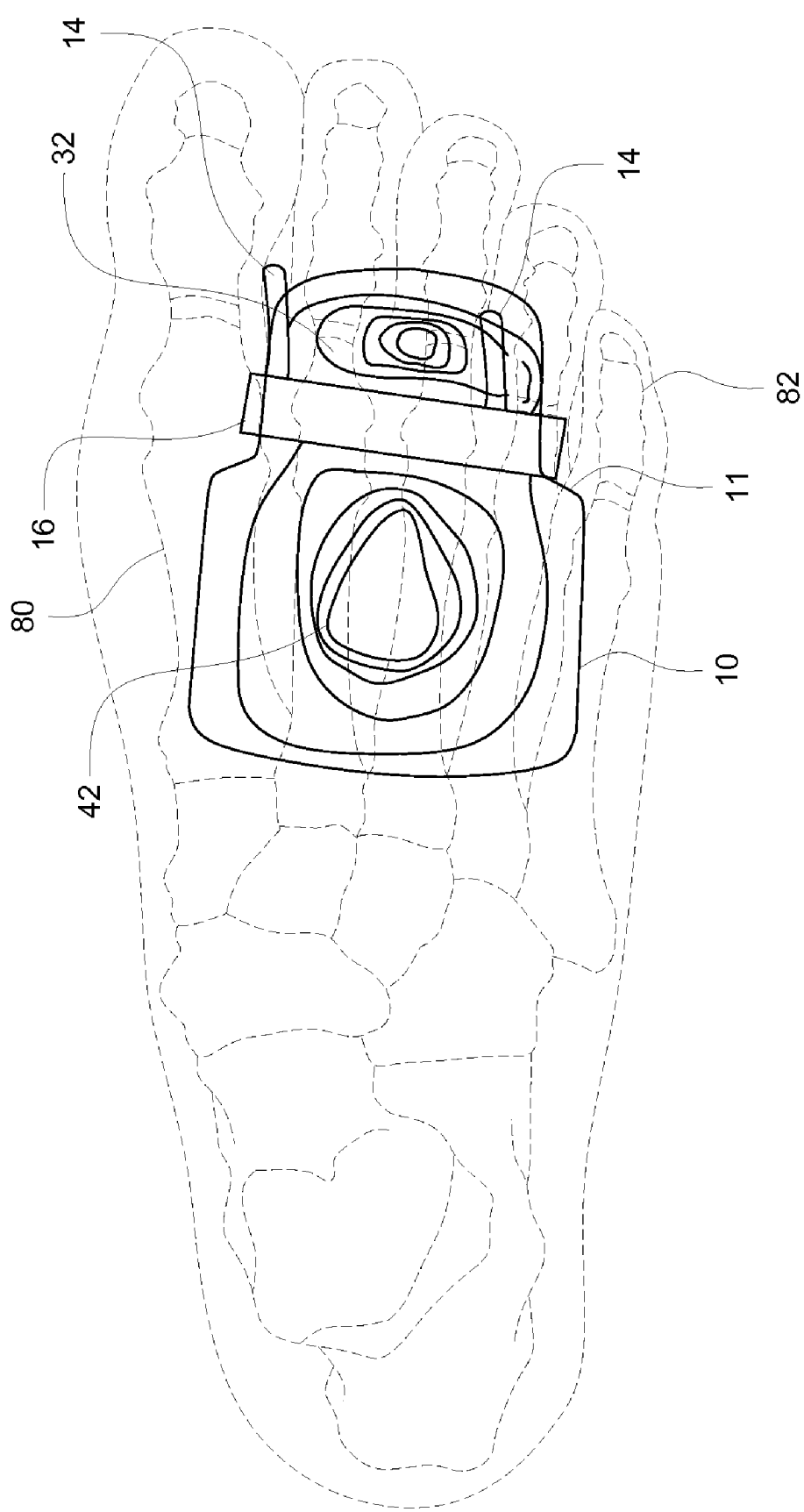
FIG. 7 illustrates a top plan view of the first and second embodiments of the present invention.
Figure 8:
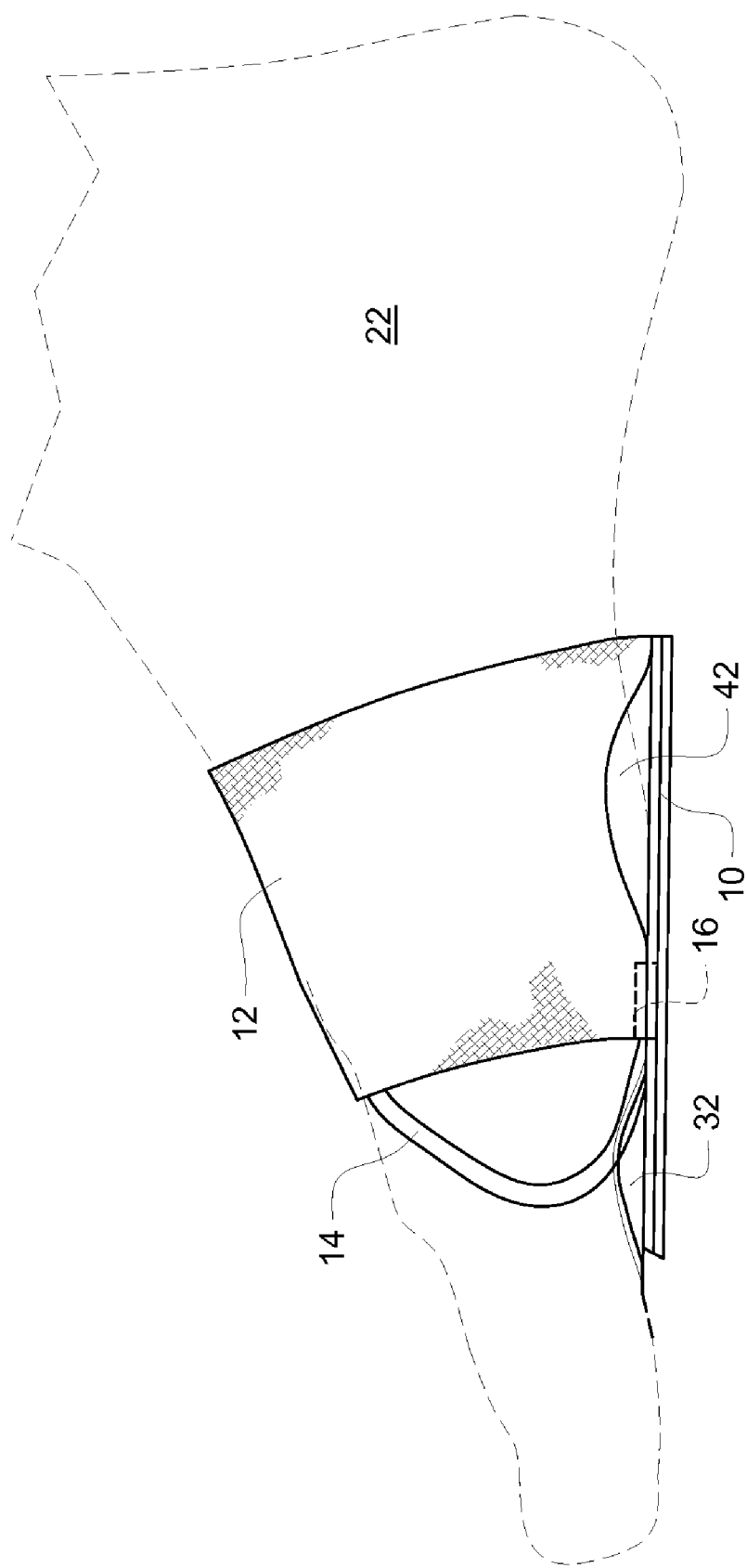
FIG. 8 illustrates a side plan view of the first and second embodiments of the present invention.

Referring to FIGS. 7 and 8, another top and side plan view of the first and second embodiments of the present invention will be described. As previously described, the magnetic platform 10 is installed in the holding strap 16 and held to the wearer's foot 22 by the elastic cloth band 12 (shown in FIG. 8). The toe straps 14 limit the amount of rotation and front/back movement of the elastic cloth band, thereby holding the magnetic platform 10 in a relatively stable position with respect to the wearer's foot 22. In the example shown in FIGS. 7 and 8, a metatarsal pad 42 is in place on the magnetic platform 10 to compensate for a problem with the third metatarsal bone and a toe crest pad 32 is in place on the magnetic platform 10 to compensate for a problem with the third phalange bone.

Figure 9:
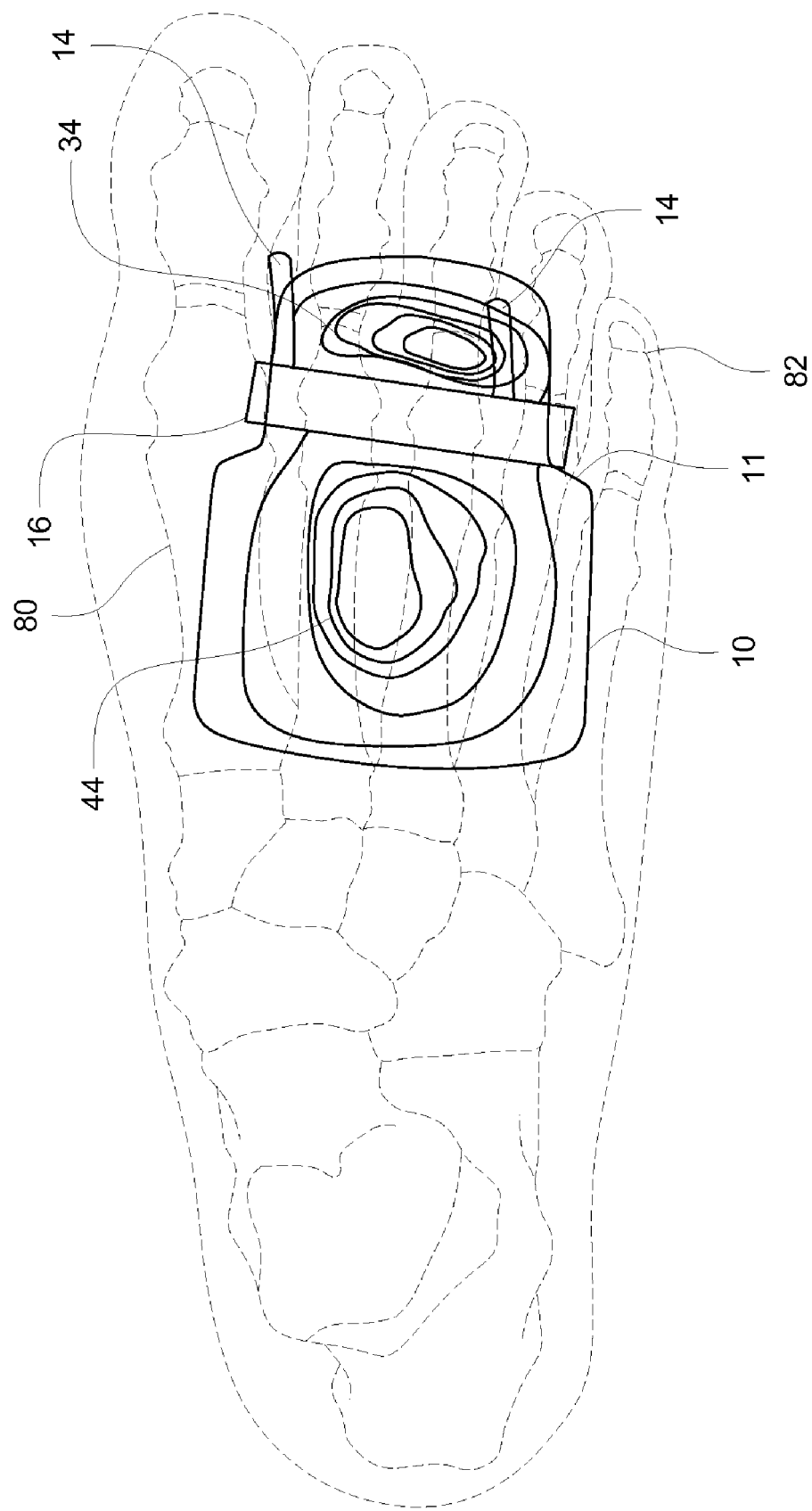
FIG. 9 illustrates a top plan view of the first and second embodiments of the present invention.
Figure 10:
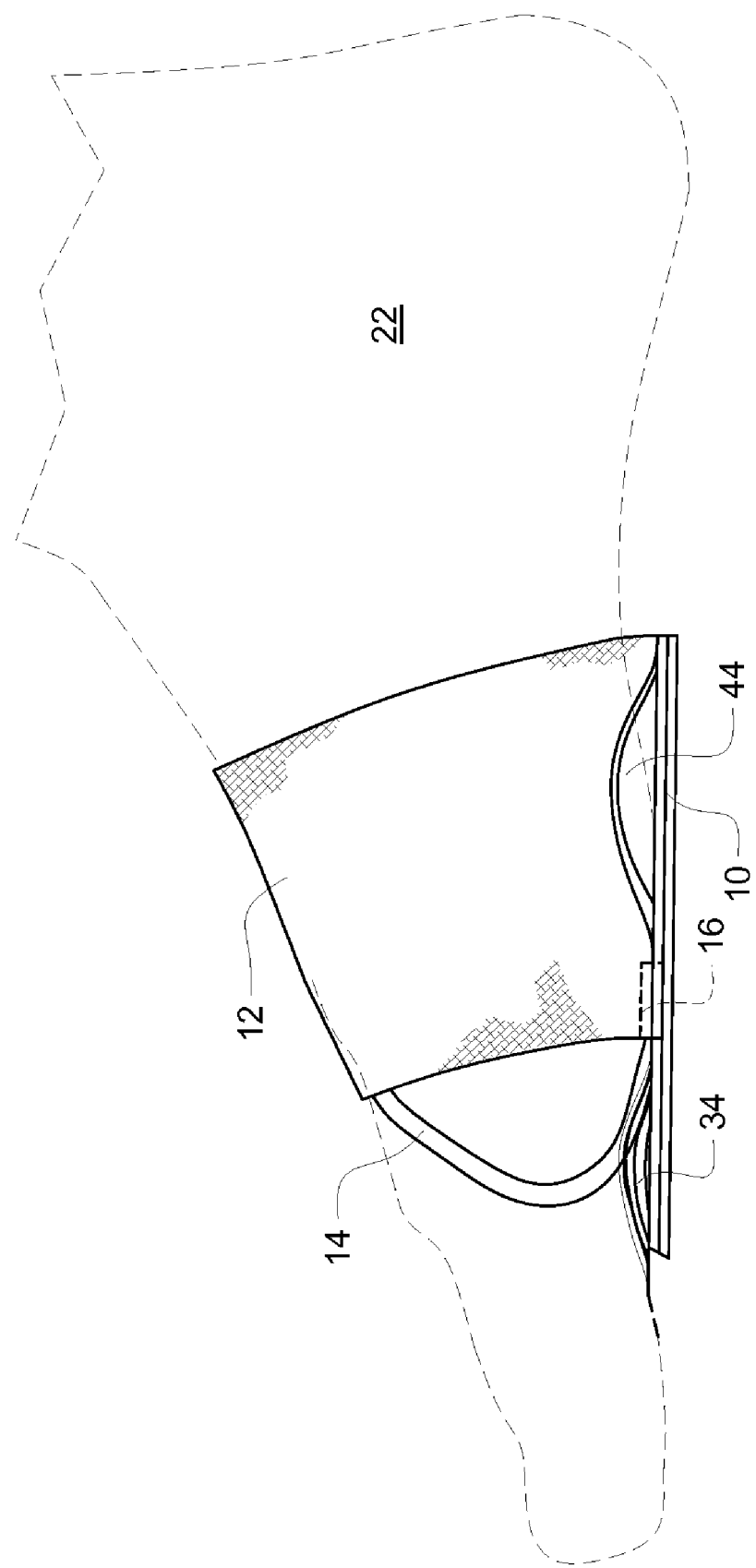
FIG. 10 illustrates a side plan view of the first and second embodiments of the present invention.

Referring to FIGS. 9 and 10, another top and side plan view of the first and second embodiments of the present invention will be described. As previously described, the magnetic platform 10 is installed in the holding strap 16 and held to the wearer's foot 22 by the elastic cloth band 12 (shown in FIG. 10). The toe straps 14 limit the amount of rotation and front/back movement of the elastic cloth band, thereby holding the magnetic platform 10 in a relatively stable position with respect to the wearer's foot 22. In the example shown in FIGS. 9 and 10, a metatarsal pad 44 is in place on the magnetic platform 10 to compensate for a problem with the second metatarsal bone and a toe crest pad 34 is in place on the magnetic platform 10 to compensate for a problem with the fourth phalange bone.

Figure 11:
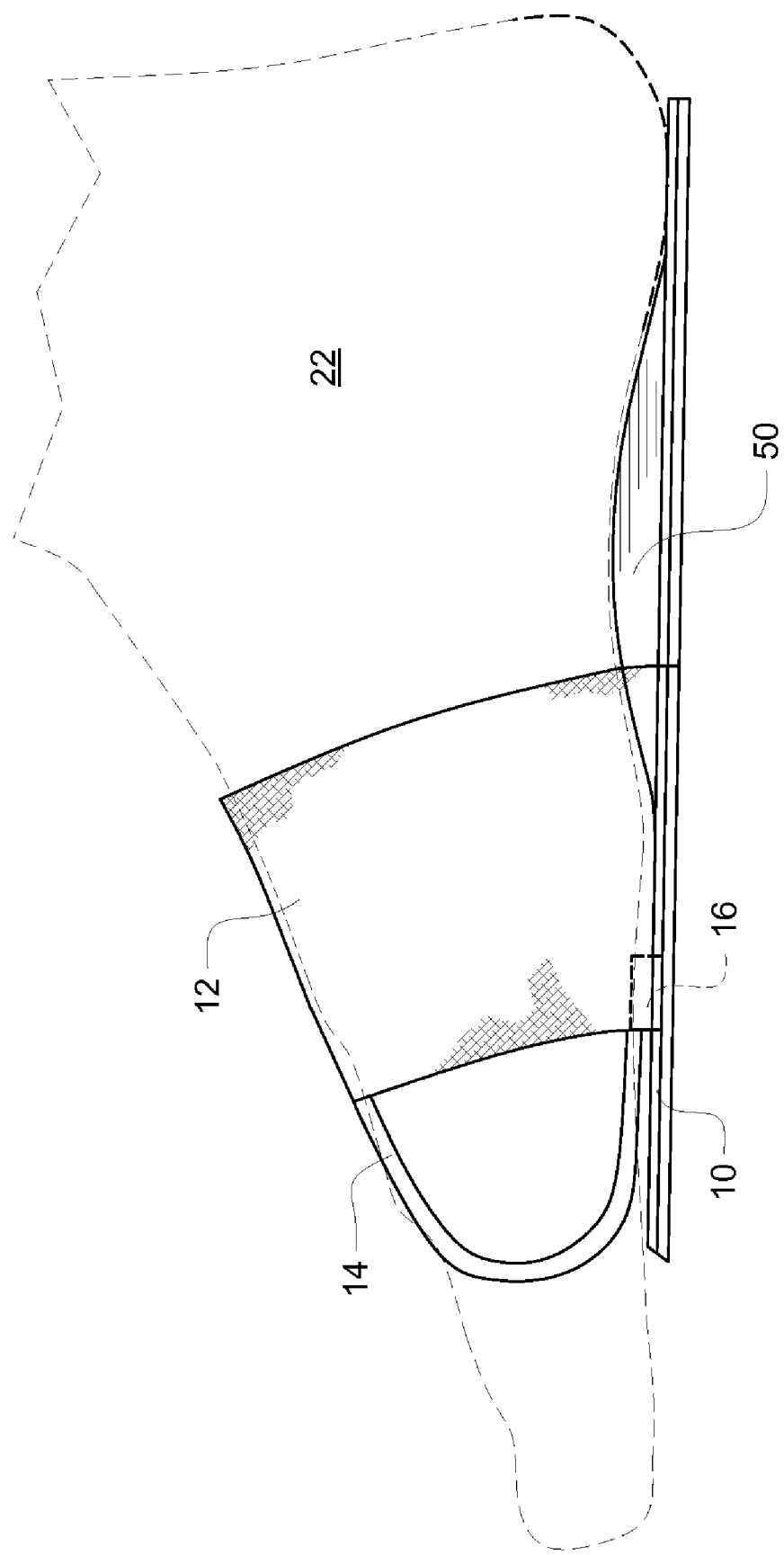
FIG. 11 illustrates a side plan view of the third embodiment of the present invention.

Referring to FIG. 11, a side plan view of the second embodiment of the present invention will be described. In this example, the magnetic platform 10 is installed in the holding strap 16 and held to the wearer's foot 22 by the elastic cloth band 12 and extends at least partially beneath the arch of the wearer's foot 22. The toe straps 14 limit the amount of rotation and front/back movement of the elastic cloth band, thereby holding the magnetic platform 10 in a relatively stable position with respect to the wearer's foot 22. In the example shown, an arch support pad 50 is in place on the magnetic platform 10 to compensate for a problem with the wearer's arches.

Figure 12:
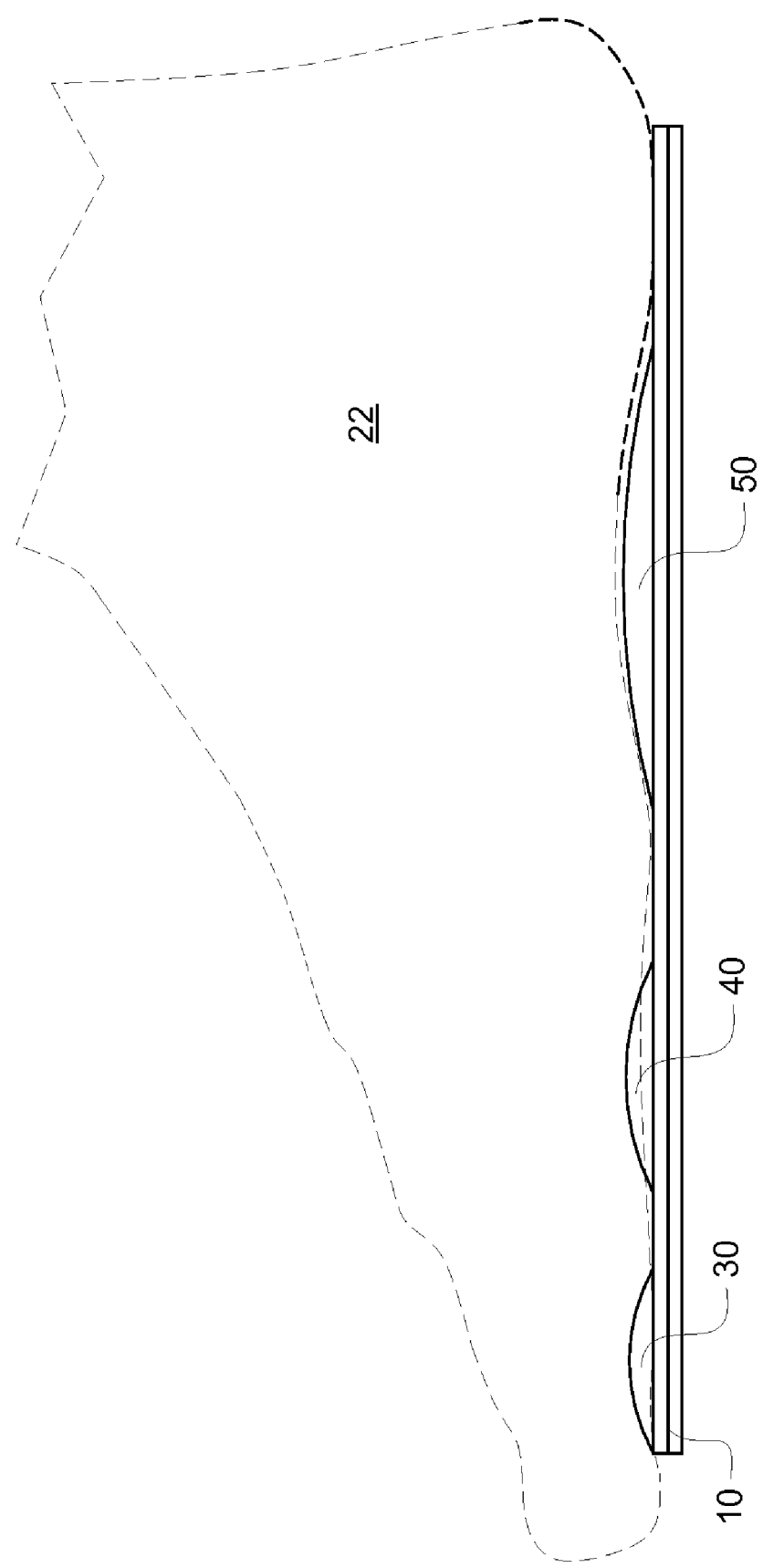
FIG. 12 illustrates a side plan view of the third embodiment of the present invention.
Figure 13:
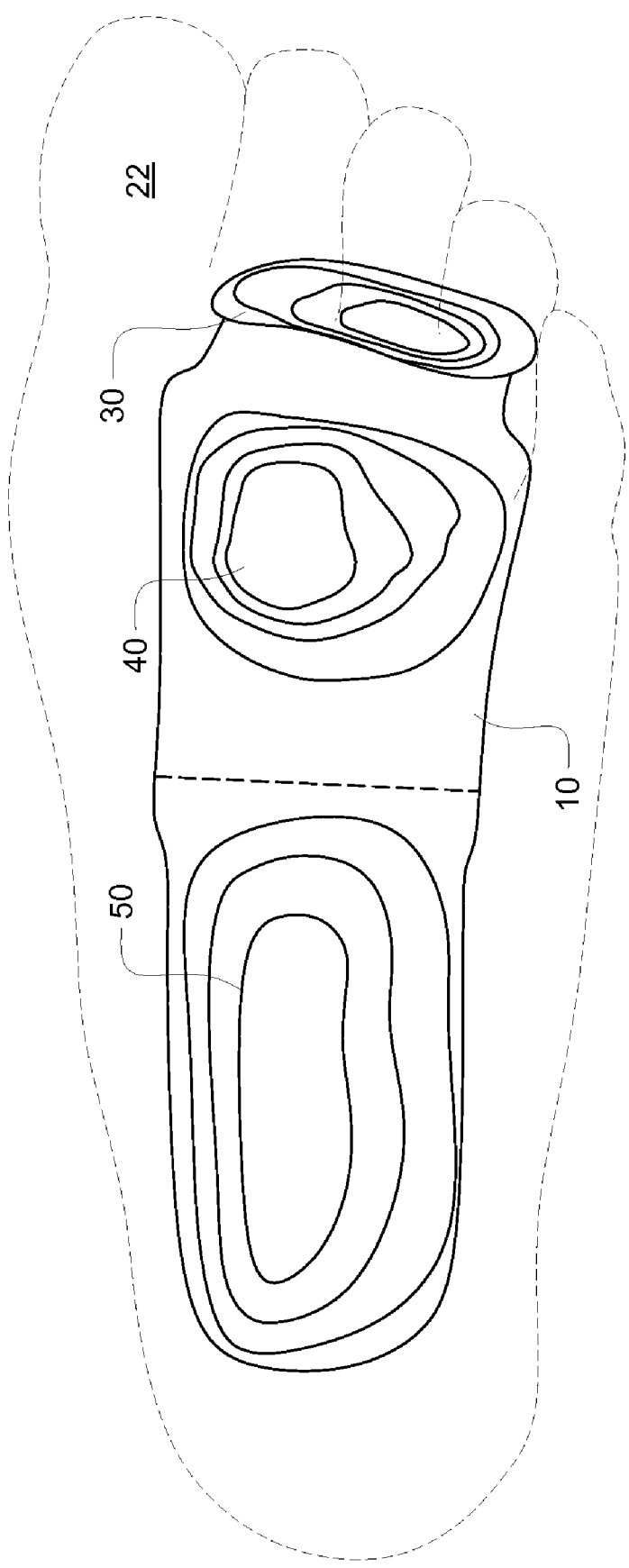
FIG. 13 illustrates a top plan view of the third embodiment of the present invention.

Referring to FIGS. 12 and 13, a side and top plan view of the third embodiment of the present invention will be described. In this embodiment, the magnetic platform 10 covers a substantial area of the inner sole of the user's shoe and is thereby held steady in relation to the shoe. Since the wearer's foot 22 is normally held steady within their shoe, this platform also holds the pads 30/40/50 in position with respect to the wearer's foot 22. In this example, a toe crest pad 30 is in place on the magnetic platform 10 for compensating for an abnormality of the second phalange bone; a metatarsal pad 40 is in place on the magnetic platform 10 to compensate for a problem with the fourth metatarsal bone; and an arch support pad 50 is in place on the magnetic platform 10 to compensate for a problem with the user's arch.

Figure 14:
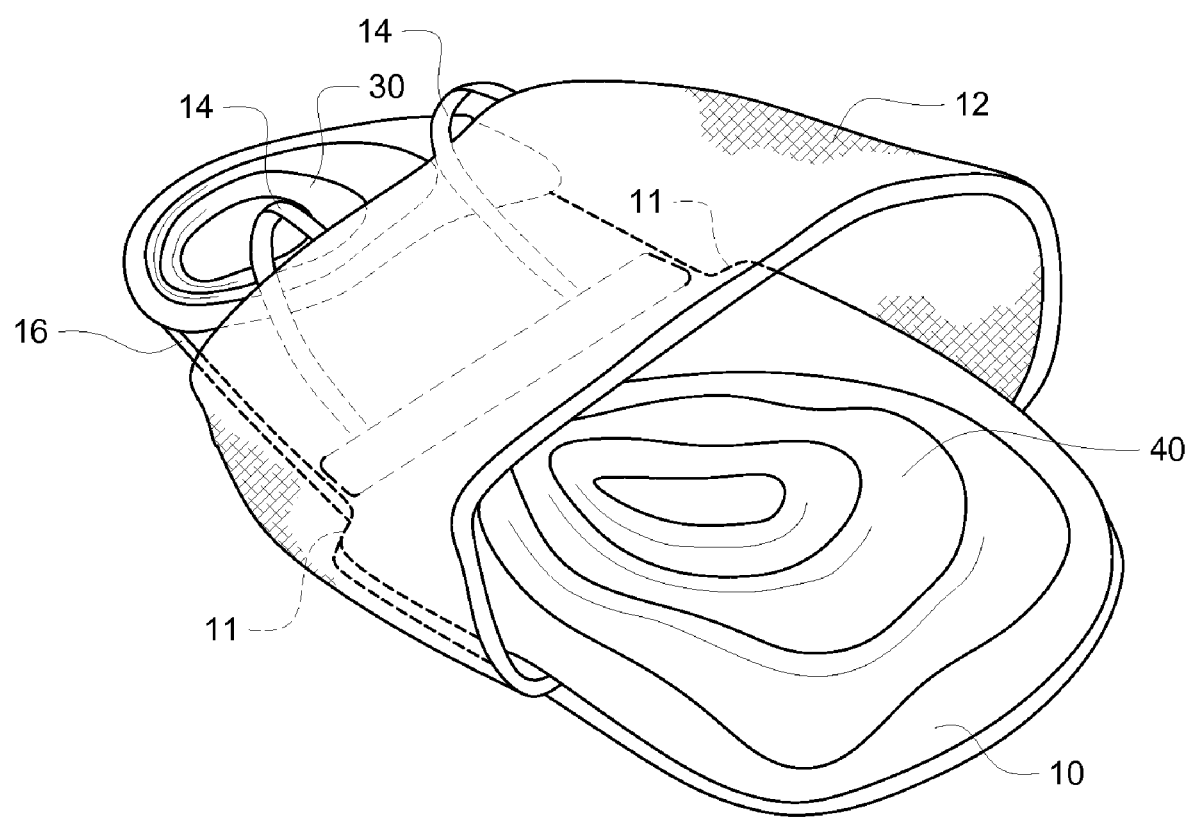
FIG. 14 illustrates an isometric view of the first embodiment of the present invention.

Referring to FIG. 14, an isometric view of the first and second embodiments of the present invention will be described. The magnetic platform 10 is attached to the elastic cloth band 12 by means known in the industry including, but not limited to sewing and gluing welding. In some embodiments, the elastic cloth band 12 completely encircles the wearer's foot while in other embodiments, the elastic cloth band 12 ends where it is affixed to the edges of the magnetic platform 10. The toe straps 14 are affixed to the upper front edge of the elastic cloth band 12 by means known in the industry including, but not limited to sewing, gluing and welding. In embodiments where the elastic cloth band 12 completely encircles the wearer's foot, the toe straps 14 are affixed to the lower front edge of the elastic cloth band 12 by means known in the industry including, but not limited to, sewing, gluing and welding. In embodiments where the elastic cloth band 12 the elastic cloth band 12 ends where it is affixed to the edges of the magnetic platform 10, the toe straps 14 are affixed to the upper surface of the magnetic platform 10 by means known in the industry including, but not limited to sewing, gluing and welding. In this example, a toe crest pad 30 and a metatarsal pad 40 are shown installed upon the magnetic platform 10.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An adjustable orthopedic device comprising:
   a platform positioned beneath a wearer's foot; and
   one or more raised pads removably affixed to the platform, whereas the one or more raised pads are manually repositionable to any X and Y coordinate on the platform; and
   a holder adapted to removably secure the platform beneath the wearer's foot, the holder comprising:

an elastic cloth band sized to encircle the wearer's foot at a location between the wearer's foot's toes and the wearer's foot's ankle; and a holding strap affixed to the elastic cloth band, the holding strap configured to securely hold the platform beneath the wearer's foot.

2. The adjustable orthopedic device of claim 1, wherein the one or more raised pads are held to the platform by magnetic force.

3. The adjustable orthopedic device of claim 2, wherein the platform is made of magnetic material and the one or more raised pads include a ferromagnetic material for holding the one or more raised pads to the platform.

4. The adjustable orthopedic device of claim 3, wherein the ferromagnetic material is steel.

5. The adjustable orthopedic device of claim 2, wherein the platform is made of magnetic material and the one or more raised pads include another magnetic material for holding the one or more raised pads to the platform.

6. The adjustable orthopedic device of claim 2, wherein the platform is made of a ferromagnetic material and the one or more raised pads include a magnetic material for holding the one or more raised pads to the platform.

7. The adjustable orthopedic device of claim 1, further comprising one or more toe straps, a first end of each toe strap affixed to an upper front edge of the elastic cloth band and a distal end of each toe strap affixed to a lower front edge of the elastic cloth band; the one or more toe straps adapted to pass between the toes of the wearer's foot, thereby keeping the holder and platform from moving significantly with respect to the wearer's foot.

8. The adjustable orthopedic device of claim 1, wherein the platform substantially covers an inner sole beneath the wearer's foot.

9. An adjustable orthopedic device comprising:

a holder configured to be worn on a wearer's foot, the holder comprising an elastic cloth band sized to encircle the wearer's foot at a location between the wearer's foot's toes and the wearer's foot's ankle;

a holding strap affixed to the elastic cloth band, the holding strap configured to securely hold the platform beneath the wearer's foot;

a platform adapted to the holder, the platform positioned beneath the wearer's foot; and a means for applying pressure to one or more bones of the wearer's foot, the means for applying pressure removably affixed to the platform through magnetic force, whereas the means for applying pressure are manually repositionable to any X and Y coordinate on the platform.

10. The adjustable orthopedic device of claim 9, wherein the platform is made of magnetic material and the means for applying pressure further comprises a ferromagnetic material for holding the means for applying pressure to the platform.

11. The adjustable orthopedic device of claim 9, wherein the platform is made of magnetic material and the means for applying pressure further comprises another magnetic material for holding the means for applying pressure to the platform.

12. The adjustable orthopedic device of claim 9, wherein the platform is made of a ferromagnetic material and the means for applying pressure further comprises a magnetic material for holding the one or means for applying pressure to the platform.

13. The adjustable orthopedic device of claim 9, further comprising one or more toe straps, a first end of each toe strap affixed to an upper front edge of the elastic cloth band and a distal end of each toe strap affixed to a lower front edge of the elastic cloth band; the one or more toe straps adapted to pass between the toes of the wearer's foot, thereby keeping the holder and platform from moving significantly with respect to the wearer's foot.

14. The adjustable orthopedic device of claim 9, wherein the platform substantially covers an inner sole beneath the wearer's foot.

15. An adjustable orthopedic device comprising:

a holder configured to be worn on a wearer's foot, the holder comprising:

an elastic cloth band sized to encircle the wearer's foot at a location between the wearer's foot's toes and the wearer's foot's ankle; and a holding strap affixed to the elastic cloth band, the holding strap configured to securely hold a magnetic platform beneath the wearer's foot, the magnetic platform includes a magnetic material; and a means for applying pressure to one or more bones of the wearer's foot, the means for applying pressure including a ferromagnetic material providing a removable adherence to the magnetic platform through magnetic force, whereas the means for applying pressure are manually repositionable to any X and Y coordinate on the magnetic platform.

16. The adjustable orthopedic device of claim 15, further comprising one or more toe straps, a first end of each toe strap affixed to an upper front edge of the elastic cloth band and a distal end of each toe strap affixed to a lower front edge of the elastic cloth band; the one or more toe straps adapted to pass between the toes of the wearer's foot, thereby keeping the holder and platform from moving significantly with respect to the wearer's foot.

17. The adjustable orthopedic device of claim 15, further comprising one or more toe straps, a first end of each toe strap affixed to an upper front edge of the elastic cloth band and a distal end of each toe strap affixed to a top surface of the platform; the one or more toe straps adapted to pass between the toes of the wearer's foot, thereby keeping the holder and platform from moving significantly with respect to the wearer's foot.

18. The adjustable orthopedic device of claim 15, further comprising a cut line adapted to the magnetic platform.

* * * * *